US008364239B2

(12) United States Patent
John et al.

(10) Patent No.: US 8,364,239 B2
(45) Date of Patent: Jan. 29, 2013

(54) METHOD FOR PROVIDING INFORMATION OF A LOCALLY RESOLVED RECONSTRUCTION QUALITY OF A TARGET VOLUME IN A THREE-DIMENSIONAL RECONSTRUCTION VOLUME PRESENTATION

(75) Inventors: Matthias John, Nürnberg (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1549 days.

(21) Appl. No.: 11/725,377

(22) Filed: Mar. 19, 2007

(65) Prior Publication Data

US 2007/0238964 A1 Oct. 11, 2007

(30) Foreign Application Priority Data

Mar. 23, 2006 (DE) ......................... 10 2006 013 473

(51) Int. Cl.
*A61B 5/05* (2006.01)

(52) U.S. Cl. ........ 600/407; 600/437; 382/128; 382/131; 382/294

(58) Field of Classification Search .................. 600/437, 600/407; 382/294, 128, 131
See application file for complete search history.

(56) References Cited

U.S. PATENT DOCUMENTS

| | | | | |
|---|---|---|---|---|
| 5,461,650 | A | 10/1995 | Tam | |
| 5,838,756 | A | 11/1998 | Taguchi et al. | |
| 6,728,424 | B1 * | 4/2004 | Zhu et al. | 382/294 |
| 2003/0052879 | A1 | 3/2003 | Barth et al. | |
| 2004/0260171 | A1 | 12/2004 | Graumann | |
| 2005/0238253 | A1 * | 10/2005 | Behrenbruch et al. | 382/294 |

* cited by examiner

*Primary Examiner* — Brian Casler
*Assistant Examiner* — Joseph M Santos

(57) ABSTRACT

The invention relates to a method and a device for locally-resolved visualization of the reconstruction quality, especially of the coverage of a target volume to be recorded as an image and reproduced in a three-dimensional reconstruction volume presentation, especially in the human body, by two-dimensional and/or three-dimensional images covering subareas of the volume recorded by a recording device arranged inside the target volume, with which the three-dimensional reconstruction volume presentation is created, with the subareas of the target volume covered by the individual images being determined and a visual locally-resolved presentation of the reconstruction quality, especially of the coverage, being created and output as a function of the subarea coverage.

19 Claims, 4 Drawing Sheets

S0 Coverage volume creation

S1 Determination of covered subareas for each image

S2 Assignment of a value to each voxel of the coverage volume

S3 Presentation of the coverage volume

Recording ended ?

no yes

End 1
2
7
8
CATHETER
CONTROL
CT DEVICE
POSITIONING
SYSTEM
6
3
4
5
PROCESSING
UNIT
9
10
26

18
23
22
21
22
19
20

24
25
16
6

METHOD FOR PROVIDING INFORMATION OF A LOCALLY RESOLVED RECONSTRUCTION QUALITY OF A TARGET VOLUME IN A THREE-DIMENSIONAL RECONSTRUCTION VOLUME PRESENTATION

CROSS REFERENCE TO RELATED APPLICATIONS

This application claims priority of German application No. 10 2006 013 473.7 filed Mar. 23, 2006, which is incorporated by reference herein in its entirety.

FIELD OF THE INVENTION

The invention relates to a method for locally-resolved visualization of the reconstruction quality, especially of the coverage of a target volume to be recorded as an image and reproduced in a three-dimensional reconstruction volume presentation, especially in the human body, by two-dimensional and/or three-dimensional images covering subareas of the volume recorded by a recording device disposed within the target volume, with which the three-dimensional reconstruction volume presentation is created.

BACKGROUND OF THE INVENTION

Recording images of parts of the body, especially hollow organs, from within and the reconstruction of the images in a 3D presentation is known from the medical field. An image recording device, generally a medical device comprising an ultrasound device or an OCT device, is introduced into the body in such cases. These medical devices, which in particular can be catheters, are then moved within the interior of the hollow organ and different two-dimensional images, mostly sectional images, or three-dimensional images are recorded at different positions and with different orientations. Three-dimensional images are also recorded if for example a recording device for recording two-dimensional images is continuously rotated. For an ultrasound device the axis of rotation can either be in the direction of the sound or at right angles to it. In the first case a three-dimensional subvolume in the shape of a sphere, in the second case a three-dimensional subvolume, the cross section of which is in the shape of a butterfly, is recorded.

A three-dimensional reconstruction volume can be created from these two-dimensional or three-dimensional recordings of partial areas of the volume of interest, in this case a hollow organ. First of all the position and orientation of the images must be established for this. In this connection two alternatives are known in particular. In one alternative the medical device can be connected to a positioning system, by which the position and orientation of the individual images relative to one another can be determined. As an alternative or in addition, it is possible for a three-dimensional first data set or a three-dimensional first reconstruction respectively to already be available, which has been recorded from outside using another modality, for example a magnetic resonance image data set or a computer tomography 3D image data set. The images can be registered with this first image data. In this way too the position or orientation respectively of the individual images relative to one another is obtained.

Areas of the target volume not covered, especially of the hollow organ, are interpolated in the usual method in this case in order to obtain a complete three-dimensional reconstruction volume. This reconstruction volume is then visually presented as a reconstruction volume presentation. Disadvantageously however, because of the interpolation, it is not possible to see from the presentation of the reconstruction volume whether all areas of interest are recorded sufficiently accurately or even recorded at all. It can thus occur that certain areas are reconstructed in lower quality or even not recorded at all, without the user being aware that this has happened.

SUMMARY OF THE INVENTION

The object underlying the invention is thus to specify a method which provides a user with additional information for three-dimensional reconstruction volume presentation.

To achieve this object there is provision in accordance with the invention for the subareas of the target volume covered by the individual images to-be determined and a visual locally-resolved presentation of the reconstruction quality, especially of the coverage, to be created and output as a function of the subarea coverage determined.

It is thus proposed in the inventive method to first determine which subarea of the target volume the individual images cover. This is possible on the basis of the position information and orientation information which can be obtained in the ways mentioned in the introduction, namely through registration with a three-dimensional first reconstruction or a positioning system or navigation system respectively, as well as from knowledge of the characteristics of the image recording device. In accordance with the invention the individual subareas can be converted directly into a locally-resolved presentation of the coverage. Especially advantageously however it is also possible to determine the reconstruction quality for each location in the reconstruction volume not only with reference to a yes-no decision, i.e. whether the area is covered by an image or not, but to create a value which also reflects the interpolation quality at this point. Thus, although a location of the reconstruction volume may not itself be covered by an image; there are many adjacent images so that there is likely to be a good interpolation which can be shown in the presentation of the reconstruction quality.

The presentation of the reconstruction quality can be output as a separate presentation within the reconstruction volume presentation itself, or in an external presentation, which will be dealt with in greater detail below.

The inventive method thus advantageously provides the person recording the images with further information which lets them recognize, on a locally-resolved basis for the overall reconstruction volume, which value the reconstruction volume presentation actually has at this point. For example information can be displayed during a medical process showing whether specific areas of a hollow organ have not been recorded, so that changes to this organ caused by disease would not be detectable for example. An image can then be recorded subsequently, or if the method is executed in real time, the image recording device can be controlled so that these areas are recorded again. In the final analysis, especially with a method executed in real time, a complete and high-quality reconstruction volume presentation is obtained, since it is possible to achieve a sufficiently dense coverage of the target volume by the subareas of the individual images.

It is of importance for the visual locally-resolved presentation of the reconstruction quality for this to be able to be placed for the user in a unique relationship with the target volume. This can be achieved in particular by the spatial arrangement of the information presented which corresponds to that in the target volume. For example in this case the previous reconstruction volume and the presentation of the reconstruction quality can be shown alongside each other in the same alignment and the same size so that it is visible at a glance where a low reconstruction quality or no coverage is present and where a high reconstruction quality or coverage is present.

In a concrete implementation of the method there can be provision for a coverage volume to be created with the dimensions of the reconstruction volume, with each voxel of the reconstruction volume being assigned to a voxel of the coverage volume, each voxel of the coverage volume being assigned a value indicating the reconstruction quality depending on the coverage, taking into account the coverage area of each image, and for the coverage volume to be at least partly shown, with the presentation being based on the values. In this case a coverage volume with the dimensions of the reconstruction volume is first created, meaning that the coverage volume covers the same area as the reconstruction volume, consequently the target volume. This is expressed by the fact that a voxel of the coverage volume is assigned to each voxel of the reconstruction volume. In this case it should be noted that a number of voxels of the reconstruction volume can be assigned to a single voxel of the coverage volume, which produces a coarsening of the presentation. This can reduce computation times where necessary.-Each voxel of the coverage volume is then assigned, taking into account the coverage area of each image, a value indicating the reconstruction quality depending on the coverage or the value indicating the coverage. This value can for example be a grayscale value or another value already able to be used later in a presentation. It is then especially simple to present the coverage volume since it principally then just represents a three-dimensional image of which the image information is the reconstruction quality, especially the coverage. The values are presented for display immediately in this variant. It is of course also possible to have the coverage volume only partly displayed, for a specific "region of interest" (ROI) for example.

The type of visual locally-resolved presentation of the reconstruction quality, especially of the coverage, can be designed in a multiplicity of ways. Initially it can prove expedient for all subareas covered by at least one image to be displayed so they can be distinguished from non-covered areas, especially the value of a complete coverage if the corresponding voxel of the reconstruction volume is covered by at least one image. A voxel is covered by an image in this case if image data is present for the location described by the voxel. This value or the form of the presentation respectively which shows a location which lies in a subarea covered by an image is then uniquely assigned to this characteristic of the location or of the voxel respectively. The subareas which are covered by images are consequently clearly recognizable in the presentation. On a gray value scale this type of presentation or the value can correspond to the deepest possible black.

Alternatively it is naturally also possible for the subareas covered by a number of images to be presented to indicate the multiple coverage, especially for a value indicating the multiple coverage to be assigned to their voxels. In this presentation it can consequently also be recognized how often a specific point in the target volume has already been recorded. The recording of images is a measurement which itself has a certain imprecision. Thus the reconstruction quality can be further improved by a multiple image recording.

In a variant in which the subareas covered by images are to be as clearly recognizable as possible, it is advantageous for areas not covered by images to be presented as the same and areas covered by images to be presented differently, especially for a voxel not covered by images to be assigned a value which is the same value for all the non-covered voxels. In the simplest case this allows a presentation to be created in which it is possible to read off the precise extent of the subareas covered by images. Where multiple coverage is displayed this can additionally be inferred as information. A simple-to-interpret presentation comprising few graduations, especially a yes-no presentation, is created. For example a voxel which is covered by at least one image can be assigned the value "1", a voxel which is not covered by an image can be assigned the value "0". This simple binary distinction can even be displayed in a black-and-white presentation.

However it is often desirable to obtain a more precise statement even about the reconstruction quality of the voxels which are not covered. Thus, in a further embodiment of the invention, there can be provision for each voxel covered by at least one image of the reconstruction volume to be assigned a grayscale sphere described by a function, especially a Gaussian sphere in the coverage volume, with the maximum grayscale value of the function lying in this voxel, after which each voxel of the coverage volume will be assigned the maximum of the greyscale values of all functions of the voxels covered by at least one image in the currently observed voxel as a value. Grayscale values in this case extend from a minimum value to a maximum value, especially from 0 to 1.1 can for example especially advantageously be selected as the maximum value. This value is then automatically assigned to each voxel covered by an image since the maximum of the grayscale sphere is to come to rest in precisely this voxel and the maximum is also selected as the greatest value at this point. Neighboring voxels then have a lower grayscale value, adjacent voxels outwards in their turn an even lower grayscale value, etc. The grayscale value specified by the grayscale value function thus drops as the distance of a voxel from a voxel covered by the image increases. This illustrates the lower reconstruction quality which can be achieved by interpolation. The Gaussian sphere which is described by a Gaussian function extended to the three-dimensional has shown itself to be particularly expressive here. Thus, according to the method, after each voxel covered by an image has been assigned a grayscale value function, each voxel of the coverage volume is again considered individually. If there is a specific number, for example n, of voxels covered by the image, n grayscale value functions f1, f2, . . . ,fn are now defined on the coverage volume. The maximum from the set of function values for this voxel, max {f1 (x, y, z), f2 (x, y, z), . . . ,fn (x, y, z)} is now determined for a voxel (x, y, z) of the coverage volume. This value is assigned to the voxel in the coverage volume. It then indicates whether the observed voxel (x, y, z) is covered (maximum grayscale value, especially 1) or how near the voxel (x, y, z) lies to the closest voxel covered by the image. The presentation of the reconstruction quality, i.e. of the coverage volume, can then also be a grayscale representation, with white meaning far away from a voxel covered by an image and black meaning coverage by an image, or vice-versa. Other types of presentation are however also conceivable which reflect a variation between a minimum and a maximum grayscale value, for example colored representations using a color spectrum, monochrome representations, height lines etc.

Such an assignment of grayscale values or values does not absolutely have to be based on a maximum of the grayscale function values. It is also conceivable for the values of the grayscale functions to be simply added for each voxel and the value distribution produced in its turn to be standardized to a grayscale distribution. Multiple coverages are also detected in this variant, however it can no longer be uniquely established whether a voxel is now actually covered by at least one image or not.

The use of a function which falls away monotonously outwards is not absolutely necessary for the grayscale sphere. If for example a grayscale function dropping away in waves from the voxel covered by an image is used, a type of height line representation can be created.

If this type of grayscale distribution has been obtained, it can be advantageous if the grayscale distribution produced is smoothed in an additional step, in order to make the presentation more convenient and easy-to-interpret in this way.

The method can be performed especially advantageously in real time. The user is thus informed during the recording as to the areas which are not or are not sufficiently detected, so that the image recording device can then be moved within the target volume to the position in which it can record the non-covered subareas of the target volume. To this end a number of further improvements are conceivable within the framework of the method, which offer further advantages in the real time variant. Provision can thus be made for the position and/or orientation of the image recording device to be shown together with the presentation of the reconstruction quality, especially with the coverage volume. The position and/or orientation of the image recording device can be presented in different ways within the presentation of the reconstruction quality. To this end it is necessary to know the position and/or orientation of the image recording device in the three-dimensional reconstruction volume. This can be achieved by a positioning or navigation system, with which the position and orientation of the image recording device is determined in a coordinate system registered with the reconstruction volume of the coordinate system. In the medical area it is also conceivable for the position and orientation to be determined from fluoroscopy images defined during the operation. Through the presentation of the position of the image recording device and the presentation of the orientation of the image recording device areas not covered or not sufficiently covered can be activated and recorded.

Particularly advantageously, in addition or as an alternative, the recording area of the image recording device can be shown together with the presentation of the reconstruction quality, especially the coverage volume. The recording area of the image recording device is the area which was covered by an image recorded at the instant in time. It can be determined from the current position and orientation of the imaging device, as described above, and for example included in the display in another color to make it easier to distinguish. This advantageously allows the user to quite explicitly create recordings in exactly the area which appears to them to have too little coverage and no coverage.

In a further embodiment of the real time process the area of coverage of at least one image, especially of the image or images last recorded, can be shown or highlighted in the presentation. The person recording the image can establish, for example when showing the coverage area of the last image recorded, whether this has actually recorded the desired area. If this is not the case they can reposition the image recording device and record a further image, from which they can once again detect whether this is filling out the gap.

In a further embodiment, with a method executed in real time, a further more general value can also be determined, which is established on the basis of the current recording area of the image recording device and specifies the improvement of the coverage or reconstruction quality respectively by recording an image in this current recording area. This value can then be presented optically and/or acoustically. Methods for determining such a further value, which determine the reconstruction quality of the overall reconstruction volume or its change on the basis of the further recording, are generally known. The user is in this case given the opportunity to detect the extent to which recording an image at the current point in time is sensible or optimal. This can also be done by acoustic encoding.

If necessary the actual "region of interest" can represent just a subarea of the target volume or the user can establish a subarea for which coverage is particularly bad. Expediently an acoustic signal can be output which indicates when the recording area of the image recording device intersects with the target volume or a selected subvolume of the target volume. The user is guided audibly, they are audibly notified whether they are at all located in a position with the image recording device in which they can record a part of the target volume. This type of specific subvolume can for example be marked interactively in a presentation by the user. The acoustic signal then specifies whether and if necessary to what extent the subvolume is contained in the recording area of the image recording device.

There are generally a number of options for outputting the presentation of the reconstruction quality. Thus provision can be made for the presentation of the reconstruction quality, especially the coverage volume, to be shown together with the reconstruction volume representation, especially in the same orientation and/or overlaid. In this case not only the reconstruction volume is shown to the user but simultaneously also the information as to the reconstruction quality available at the corresponding position. The presentation of the reconstruction quality, especially the coverage volume, can in this case for example be overlaid in another color. The user recognizes immediately which areas of the target volume are of interest and how well these have been detected by the previous images. In particular, if the method is being executed in real time, they can then activate a position in the target volume, from which they can then record further images of this sub-volume of interest with the image recording device or they can start again with a new series of recorded images.

As an alternative or in addition, it is also possible for a previously recorded three-dimensional first reconstruction to be registered with the coverage volume and for the first reconstruction or image data derived from this to be shown with the coverage volume, especially in same orientation and/or overlaid. In this case a presentation is possible in a high-resolution anatomy known from a three-dimensional first reconstruction, which, especially with a method executed in real, time, allows precise navigation or determination of the areas still to be recorded or to be better recorded. In particular such a first reconstruction presentation, which was recorded for example with a magnetic resonance system or a computer tomograph, can be displayed with the presentation of the reconstruction quality from the beginning of a series of recordings, so that it can be observed how the reconstruction volume is filled slowly by the image recordings and the target volume covered.

With particular advantage values assigned to specific voxels can be represented as transparent or not shown at all and/or different values can be assigned a different transparency in the presentation. This means that recognizability is ensured in an overlay presentation.

A further increase in the information density of the presentation of the reconstruction quality can be achieved by boundaries representing subareas being shown. It is naturally also possible to draw in the boundaries of each partial area, which is shown by an image.

In the case already mentioned, in which only a subvolume of the target volume forms the actual ROI, this subvolume of the target volume can be selected and the reconstruction quality can be presented only for this subvolume. If for example only an image of the right chamber of a heart is to be recorded, the target volume can still be the heart, but the subvolume is the right heart chamber. In the final analysis only the relevant information is shown.

An ultrasound imaging device can be used as the imaging device, especially in the case of recordings of the human body. Medical equipment and devices, especially catheters, with ultrasound imaging apparatus and also their benefits in the medical engineering field are known.

It should finally be pointed out that provision can be made to enable users to manipulate the presentation of the reconstruction quality to adapt it to their requirements. It is thus possible to rotate the presentation and to view it from different sides. Users can also adapt presentation options and for example select sections from which a two-dimensional presentation is obtained.

BRIEF DESCRIPTION OF THE DRAWINGS

Further advantages and details of the invention are obtained from the exemplary embodiments described below as well as on the basis of the diagrams. The figures show.

DETAILED DESCRIPTION OF THE INVENTION

Figure 1:
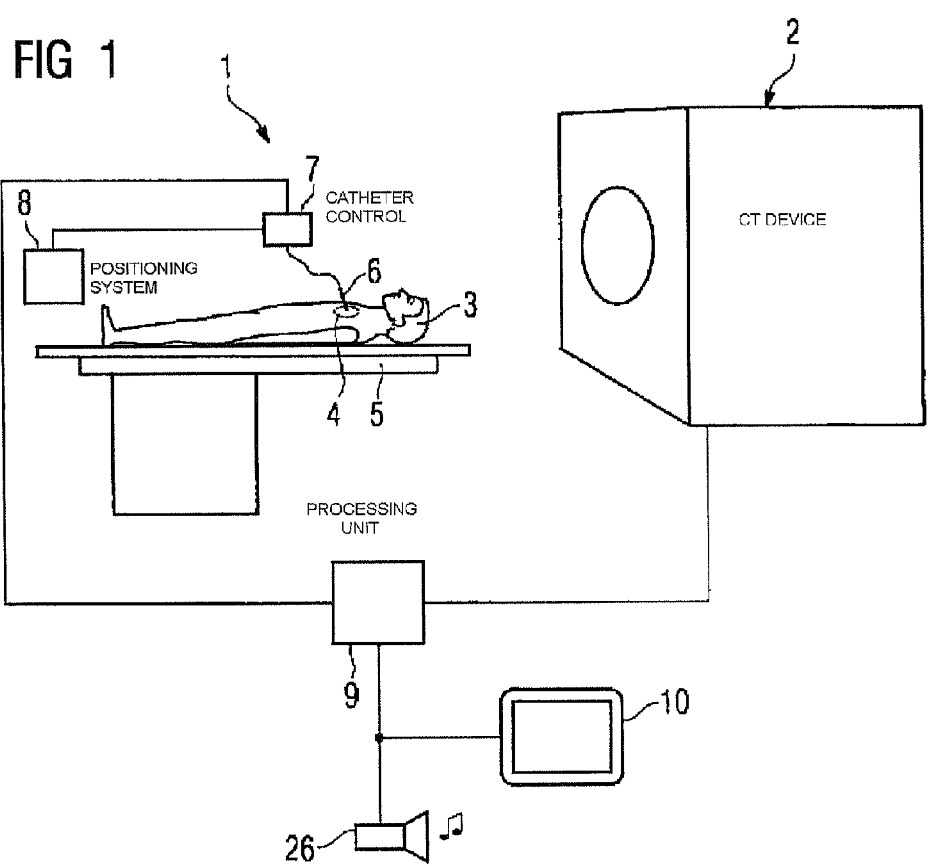
FIG. 1 A medical examination device suitable for executing the inventive method, FIG. 2 a flowchart of the inventive method, FIG. 3 a basic diagram of a one-dimensional coverage volume with grayscale functions depicted, FIG. 4 a 3D presentation of the heart with areas covered by images, FIG. 5 a basic diagram of a presentation with a first reconstruction or with the reconstruction volume, and FIG. 6 a diagram of the recording area of the image recording device, of the image recording device and of the last image coverage area recorded in a first reconstruction diagram or the reconstruction volume presentation respectively.

FIG. 1 shows a medical examination apparatus 1. In this case pre-operative images of a patient 3 can be recorded in a computer tomography device (CT device) 2. The pre-operative images, which show a target volume within the patient 3, can be further processed into a three-dimensional first reconstruction. Specific characteristics or anomalies of hollow organs can however not be detected on computer tomography images. This requires a further examination of the patient 3, with images able to be recorded within their body in the target volume 4. During this intervention the patient 3 is located on a patient bed 5. A catheter,6 with an image recording device, here an ultrasound device, is introduced into the target volume 4 in the patient 3. The image recording device of the catheter 6 can be controlled via a catheter control device 7 and two-dimensional or three-dimensional images can be recorded inside the patient 3. Using a positioning system 8, position and orientation of the catheter 6 within the patient 3, especially in the target volume 4, can be determined and transmitted to the catheter control device 7, where the data can be assigned to a recorded image. The catheter control device 7 as well as the CT device 2 are connected to a processing unit 9 to which a monitor 10 is assigned. From the images recorded by the image recording device of the catheter 6, by means of the positioning and orientation information obtained through the positioning system 8 as well as if necessary also through registration with CT data of the CT device 2, a three-dimensional reconstruction volume can be created within the catheter control device 7 or the processing unit 9 which reproduces the target volume 4. The processing device 9 is also embodied for locally-resolved determination of the reconstruction quality, especially the coverage and to present this.

Figure 2:
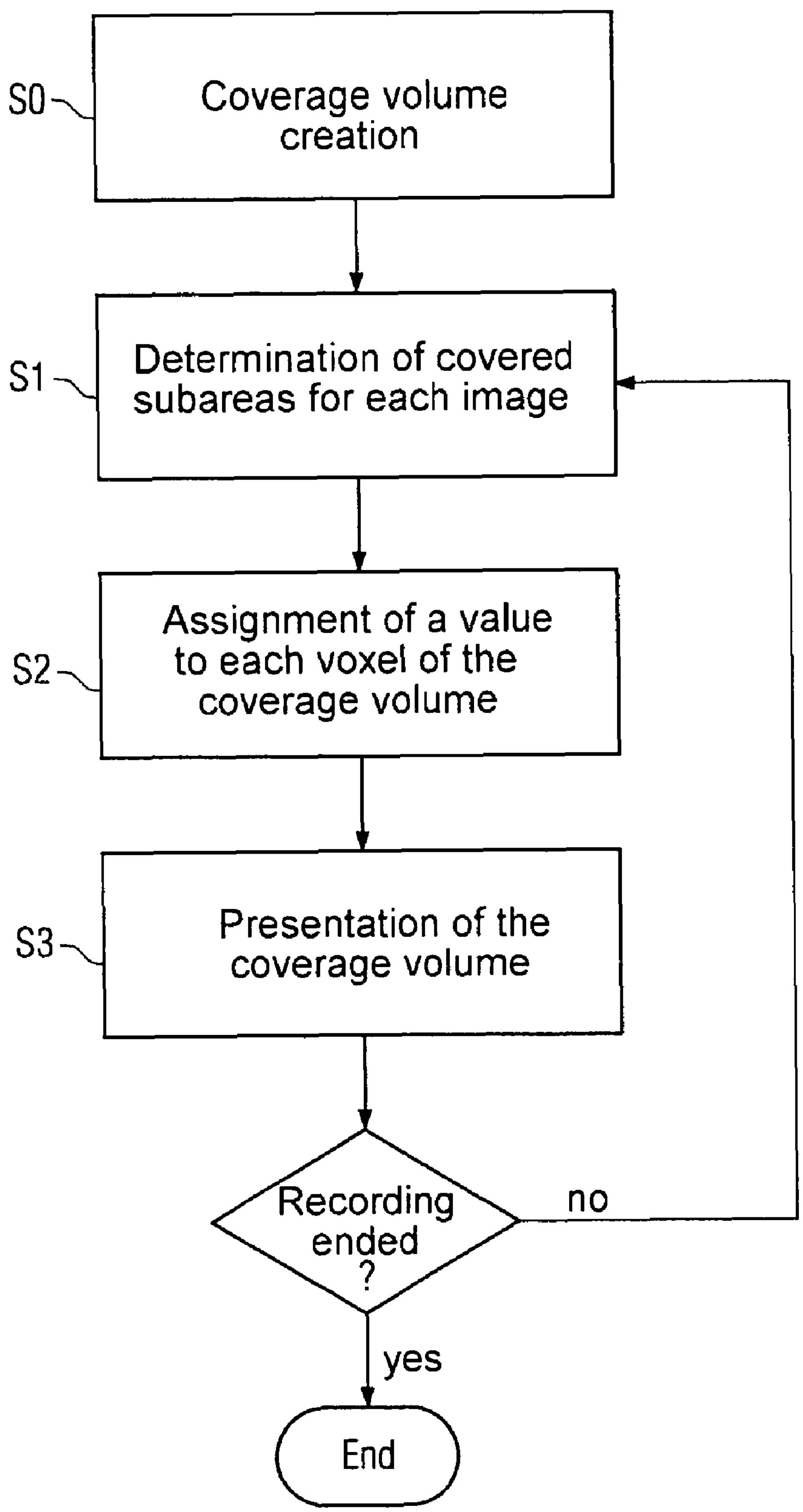

FIG. 2 shows a flowchart of the inventive method. The method is executed in real time. To execute the method it is also of advantage to know how the recording area of the image recording device of the catheter 6 extends as a function of the position and orientation, which means which areas can be seen on the recorded image.

The method takes place in the real time environment, which means that it is continuously repeated and the presentation is updated. The images are recorded in parallel in the back-ground.

First, in step S0, before the repeating steps, a coverage volume is created, with a voxel of the coverage volume being assigned to each voxel of the reconstruction volume. In this exemplary embodiment this is a 1:1 assignment. The coverage volume—like the reconstruction volume—consists of a set of voxels which are identified by the entry (x, y, z) in a coordinate system and are thus assigned a location in a later image presentation. The content of a voxel corresponds in the reconstruction volume to the reconstructed image information at the location designated by the voxels (x, y, z). For the sake of simplification the voxel labels (x, y, z) used are the same because of the 1:1 assignment for both the coverage volume and also the reconstruction volume. In the final analysis it can also be said that a voxel (x, y, z) of the reconstruction volume contains the reconstructed, if necessary interpolated picture information, the corresponding voxel (x, y, z) of the coverage volume after execution of the method contains a value for the reconstruction quality at this location. The values stored in the coverage volume are then used later for the presentation as a type of image information. The method now involves assigning values to the voxels (x, y, z) of the coverage volume which are designed to reflect the reconstruction quality of the corresponding image data in the voxel (x, y, z) of the reconstruction volume.

In step S1 for each recorded image of the image recording device of the catheter 6, the subarea of the target volume 4 covered by the image is determined. This can be undertaken in two ways here. In one the corresponding subarea of the target volume 4 can be defined from the known position and orientation of the image recording device. In the other alternative the respective image is registered with the pre-operative first image data set and its position determined in this way.

In the final analysis the determination of covered subareas for each image is to be seen in this exemplary embodiment as determining, for each voxel of the reconstruction volume and thus for each voxel of the coverage volume, whether there is original image information available for the corresponding location in the target volume for this voxel from the image currently being considered which is to be included in the image data. The total of all these voxels which are detected by the image currently being considered forms the subarea covered for this image. All subareas of all images together then form the set of the covered voxels.

In step S2 a value is then assigned to each covered voxel of the coverage volume which describes the reconstruction quality at this voxel. Two embodiments should be considered in greater detail here.

Certainly the most simple method is for each voxel from the set of covered voxels (since each voxel of the reconstruction volume is assigned to voxel of the coverage volume with the same label, the actual distinction of the set to which the voxels belong can be ignored in most cases) to be assigned the value 1 for "covered", all remaining voxels to be assigned the value "0" for "not covered". This creates an easier representation method below but generates a lower density of information.

Figure 3:
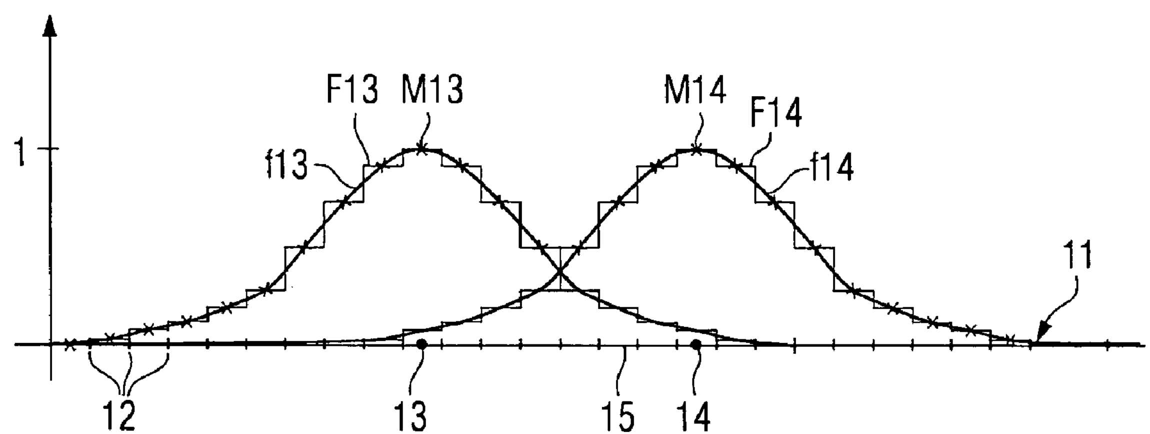

An alternative determination option for the values is to use functions which reproduce a grayscale sphere. The underlying concept is explained in greater detail in FIG. 3. To allow a simple explanation a one-dimensional reconstruction volume/coverage volume is assumed there which is symbolized by the line 11. The line divisions 12 are intended to indicate the limits of the individual voxels through which the line runs. At positions 13 and 14 along this line there is a voxel present from the set of the voxels covered by images. Thus original image data of the corresponding location in the target volume is present in the reconstruction volume at this point. Grayscale functions f13 and f14 are now assigned to the voxel 13 and the voxel 14. The maxima M13 and M14 of the functions f13 and f14 lie in the voxels 13 or 14 respectively in this case. Functions f13 and f14 are Gaussian functions in this case. They decrease monotonously as the distance from voxel 13 increases. Functions f13 and f14 have a value for each voxel which is indicated by the control functions F13 and F14. This value lies between 0 and 1. For assignment of a value to a voxel the maximum of the functions F13 and F14 is then taken for the respective voxel. It should be pointed out here that there are naturally far more than two functions present with many images. In the three-dimensional the maxima of these functions then also generally do not all lie on one line. In this example however only two functions are referred to since a simpler explanation of the underlying methodology is obtained in this way.

If we first consider voxel 13, in which the maximum M13 of the function F13 lies, with the function F14 having already almost reached 0 at this point. Consequently the value 1 is assigned to the voxel 13. The value 1, that is the maximum value, then also directly designates with this variant the voxels for which original image data is present, i.e. the voxels from the set of voxels covered by an image. The same then naturally applies to the voxel 14, in which case the function value of the function F14, again 1, is selected. An intermediate voxel 15 is considered as a last example. Here the values of the function F13 and F14 both lie between 0 and 1, but the value of function F14 is greater. This value is selected accordingly here. The selected values are identified in FIG. 3 by "x".

In this variant of the assignment of a value, each voxel of the coverage volume is thus assigned a value between 0 and 1. In the final analysis this value shows how near the voxel lies to the closest voxel covered by an image. In this case the value 1 means that this voxel is covered by an image. The proximity to the original image data also determines the quality of the interpolation, that is of the reconstruction.

In step S3, again referring to FIG. 2, the coverage volume is then displayed. If the recording of the images is declared to be finished, the method also ends. Otherwise, as soon as a new image has been recorded, the values in the coverage volume are updated.

There is a plurality of options for representing the coverage volume and thereby the reconstruction quality, especially the coverage, and a few of these options will be described below.

Figure 4:
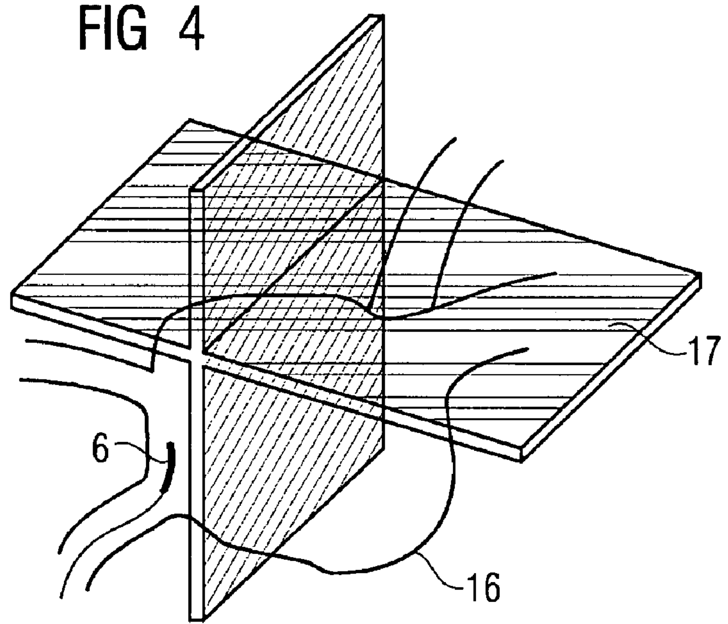

FIG. 4 shows an option for three-dimensional presentation of the coverage volume together with a heart 16 reconstructed from a pre-operative first image data set. To simplify the diagram it is assumed that only two images have been recorded here. The subareas covered by these images are overlaid at 17 as transparent presentation of the coverage of the reconstruction of the heart 16. To create such a presentation it is sufficient to assign a fixed value to each voxel of the coverage volume covered by an image, for example the value 1, and to assign another value, for example the value 0, to each voxel of the coverage volume not covered by an image. For each voxel a check is then made as to whether it is covered, meaning whether the value assigned to it is 1. If this is so, a transparent marking, if necessary in another color, is added in the correct location at the corresponding position in the three-dimensional reconstruction of the heart. The diagram shown in FIG. 4 can be rotated, meaning that it can be viewed from all sides. This means that a user can recognize immediately the places at which images are already recorded or the areas which have not been adequately covered thus far. In addition part views can be selected or cross sections can be viewed. In addition, in the diagram shown in FIG. 4, the catheter 6 is shown with an image recording device, of which the position and orientation are obtained by the positioning system 8. The presentation is refreshed in real time, so that the user can always see where there are already recordings, which areas are to be recorded in greater detail, and where the image recording device is located or the position to which it must be moved respectively.

Figure 5:
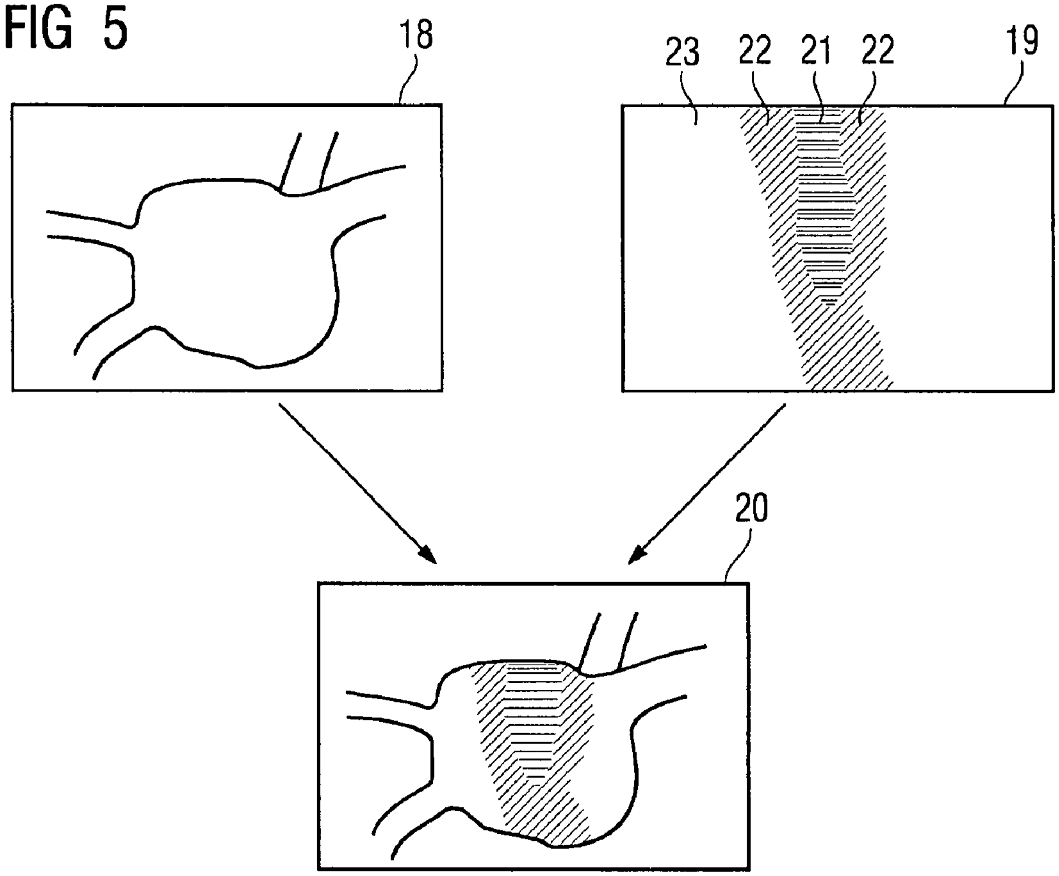

FIG. 5 shows a basic diagram for presenting the reconstruction quality together with a first reconstruction or the reconstruction volume, as it has been reconstructed previously. A pre-operative reconstruction 18 or the reconstruction volume are overlaid in this case with the coverage volume 19 into a presentation 20. In this case two-dimensional cross sections are shown here in each case. The dark area 21 in the coverage volume in this diagram means an excellent reconstruction quality. The gray area 22 represents areas of average reconstruction quality not covered by images. The white areas 23 are areas not covered by images in which reconstruction quality is bad.

Figure 6:
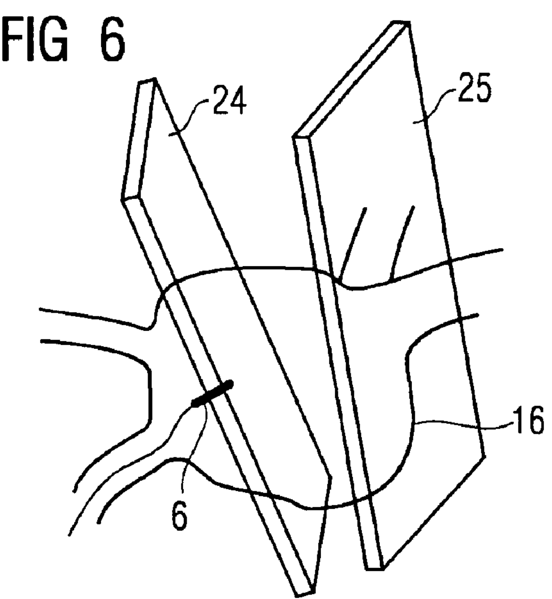

FIG. 6 finally shows a presentation of the recording area of the image recording device, of the image recording device and of the subarea of the last recorded image in a first reconstruction of the reconstruction volume respectively. In this case the information relating to the reconstruction quality is not shown in order to simplify the diagram, but normally this is also overlaid. The diagram again shows the heart 16, with the catheter 6 inside it. The overlaid rectangular solid 24 represents the instantaneous recording area of the image recording device of the catheter 6. If an image is now recorded, this would cover the area marked by the rectangular solid 24. The rectangular solid 25, which is shown in another color, represents the subarea of the target volume covered by the last image. Also shown is the locally-resolved information for reconstruction quality -not included in the diagram to improve clarity. This provides user with all the information needed for planning further imaging. The areas of the target volume which have not yet been recorded can be recognized for example and the catheter 6 or the recording area visualized by the rectangular shape 24 can be oriented so that these areas are recorded. It can then be seen from rectangular shape 25 whether the image is lying correctly.

Further display options are also conceivable. Thus there can be an acoustic output of the improvement of the general reconstruction quality in the target volume as a function of the recording area of the image recording device. It is also possible to acoustically indicate whether the current recording area of the image recording device lies in the target volume. A loudspeaker 26 assigned to the monitor 10 enables the sound to be output, see FIG. 1.

The invention claimed is:

1. A method for providing information of a locally resolved reconstruction quality of a target volume comprising a subarea in a three-dimensional reconstruction volume presentation, comprising:

recording a first image of the target volume by an imaging recording device disposed within the target volume, which is in a body of a subject undergoing a medical examination;

creating a three-dimensional reconstruction volume presentation from a plurality of images acquired by the imaging recording device, prerecorded by way of another imaging modality or both, wherein the first image and the three-dimensional reconstruction volume are spatially registered relative to one another;

determining spatial imaging-coverage in the three-dimensional reconstruction volume of at least a portion of the target volume, the spatial imaging-coverage indicative of at least an area of the target volume not recorded by the imaging recording device in the first image of the target volume;

wherein the spatial imaging coverage volume is created with a dimension of the three- dimensional reconstruction volume, wherein a voxel of the coverage volume is assigned to a voxel of the three-dimensional reconstruction volume, wherein the voxel of the coverage volume is assigned a value indicating reconstruction quality depending on the imaging-coverage determination, and wherein the coverage volume is presented at least partly with the three-dimensional reconstruction volume presentation based on the assigned value;

wherein the assigned value is a grayscale value described by a function, wherein a maximum grayscale value of the function lying in the voxel is assigned to the voxel;

creating the information of the locally resolved reconstruction quality of the three-dimensional reconstruction volume based on the determining of the spatial imaging-coverage;

outputting the information of the reconstruction quality of the three-dimensional reconstruction volume; and based on the information of the reconstruction quality, repositioning in real-time the imaging recording device within the target volume to record at least a further image of the target volume to record said at least area of the target volume not previously recorded by the imaging recording device.

2. The method as claimed in claim 1, wherein the outputting of the information of the reconstruction quality of the three-dimensional reconstruction volume comprises presenting imaging-coverage of the target volume recorded in the first image and wherein the imaging-coverage is presented or highlighted in a presentation of the first image.

3. The method as claimed in claim 1, wherein the information of the reconstruction quality of the three-dimensional reconstruction volume is created in a real time and is outputted together with a further information selected from the group consisting of: a position of the image recording device, an orientation of the image recording device, and a recording area of the image recording device.

4. The method as claimed in claim 3, wherein data effective to improve the imaging-coverage in the three-dimensional reconstruction volume is generated based on the recording area of the image recording device, and wherein said data is outputted optically or acoustically.

5. The method as claimed in claim 3, wherein data effective to indicate an intersection of the recording area of the image recording device with the target volume or a selected subvolume of the target volume is outputted.

6. The method as claimed in claim 1, wherein the information of the reconstruction quality of the three-dimensional reconstruction volume is presented jointly with the three-dimensional reconstruction volume representation, and wherein the information of the reconstruction quality of the three-dimensional reconstruction volume is presented in a same orientation with the three-dimensional reconstruction volume representation or is overlaid with the three-dimensional reconstruction volume representation.

7. The method as claimed in claim 1, wherein the plurality of images is recorded by the image recording device, wherein the portion of the target volume is covered by the plurality of images and is presented in the presentation of the three-dimensional reconstruction volume, and wherein a value indicating a multiple coverage in the plurality of images is assigned to at least one voxel of the portion of the target volume.

8. The method as claimed in claim 1, wherein a portion of the target volume covered by the three-dimensional reconstruction volume is distinguished from a non-covered portion in the three-dimensional reconstruction volume presentation and at least one voxel of the covered portion is assigned a value.

9. The method as claimed in claim 1, wherein a portion of the target volume not covered by the three-dimensional reconstruction volume is distinguished from a covered portion in the three-dimensional reconstruction volume presentation and at least one voxel of the not covered portion is assigned a value.

10. The method as claimed in claim 1, wherein a grayscale distribution of the function is smoothed, and wherein the function is a Gaussian sphere function.

11. The method as claimed in claim 1, wherein a previously recorded three-dimensional first reconstruction of the target volume is registered with the coverage volume, wherein the first reconstruction or image data derived from the first reconstruction is displayed with the coverage volume, and wherein the first reconstruction or image data derived from the first reconstruction is displayed in a same orientation with the coverage volume or is overlaid with the coverage volume.

12. The method as claimed in claim 11, wherein position and orientation of the three-dimensional reconstruction volume relative to the first image is obtained from the registration or from a positioning device connected to the image recording device.

13. The method as claimed in claim 1, wherein the assigned value is presented transparently in the presentation.

14. The method as claimed in claim 1, wherein a boundary of the portion of the target volume covered in the three-dimensional reconstruction volume is outlined in the three-dimensional reconstruction volume presentation.

15. The method as claimed in claim 1, wherein a subvolume of the target volume is selected and the information of the reconstruction quality of the three-dimensional reconstruction volume is only created for the selected subvolume.

16. The method of claim 1, wherein the determining of the imaging-coverage in the three-dimensional reconstruction volume of said at least portion of the target volume comprises determining quantitative imaging-coverage, qualitative image coverage or both.

17. A device for providing information of a locally resolved reconstruction quality of a target volume comprising a sub-area in a three-dimensional reconstruction volume presentation, comprising:

an image recording device configured to record a first image of the target volume disposed within the target volume, which is in a body of a subject undergoing a medical examination; and a processing unit configured to:

create a three-dimensional reconstruction volume presentation from a plurality of images acquired by the imaging recording device, prerecorded by way of another imaging modality or both, wherein the first image and the three-dimensional reconstruction volume are spatially registered with respect to one another, determine spatial imaging-coverage in the three-dimensional reconstruction volume of at least a portion of the target volume, the spatial imaging-coverage indicative of at least an area of the target volume not recorded by the imaging recording device in the first image of the target volume, wherein the spatial imaging coverage volume is created with a dimension of the three-dimensional reconstruction volume, wherein a voxel of the coverage volume is assigned to a voxel of the three-dimensional reconstruction volume, wherein the voxel of the coverage volume is assigned a value indicating reconstruction quality depending on the imaging-coverage determination, and wherein the coverage volume is presented at least partly with the three-dimensional reconstruction volume presentation based on the assigned value;

wherein the assigned value is a grayscale value described by a function, wherein a maximum grayscale value of the function lying in the voxel is assigned to the voxel;

create the information of the locally resolved reconstruction quality of the three-imensional reconstruction volume based on the determination of the spatial imaging-coverage, and output the information of the reconstruction quality of three-dimensional reconstruction volume, wherein, based on the information of the reconstruction quality, the imaging recording device is repositioned in real-time within the target volume to record at least a further image of the target volume to record said at least area of the target volume not previously recorded by the imaging recording device.

18. The device as claimed in claim 17, wherein the imaging recording device is an ultrasound imaging device.

19. The device as claimed in the claim 17, wherein position and orientation of the first image is obtained from a positioning device connected to the image recording device or from registering the first image with a previously recorded three-dimensional first reconstruction of the target volume.

* * * * *